United States Patent
Araki et al.

(10) Patent No.: US 7,137,735 B2
(45) Date of Patent: *Nov. 21, 2006

(54) X-RAY EQUIPMENT WITH CASSETTE STORAGE BOX LOCKING MEANS

(75) Inventors: Tatsuya Araki, Omihachiman (JP); Kimihiro Takahama, Ibaraki (JP); Hiroshi Miyata, Kyoto (JP); Mitsuhiro Hashimoto, Kyoto (JP); Toshiaki Nakamura, Nagaokakyo (JP); Takahiro Kamitake, Osaka (JP)

(73) Assignee: Shimadzu Corporation, Kyoto (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/673,386

(22) Filed: Sep. 30, 2003

(65) Prior Publication Data
US 2004/0066899 A1  Apr. 8, 2004

(30) Foreign Application Priority Data
Oct. 4, 2002  (JP) .............................. 2002-292599

(51) Int. Cl.
*G03B 42/02* (2006.01)

(52) U.S. Cl. ...................................... 378/167; 378/172

(58) Field of Classification Search ................ 378/102, 378/167, 172, 173, 174, 181, 197, 198, 204, 378/210; 250/589
See application file for complete search history.

(56) References Cited

U.S. PATENT DOCUMENTS 5,138,160 A * 8/1992 Shimizu et al. ............. 250/589
6,126,314 A * 10/2000 Morasse ..................... 378/167

* cited by examiner

*Primary Examiner*—Edward J. Glick
*Assistant Examiner*—Chih-Cheng Glen Kao
(74) *Attorney, Agent, or Firm*—Manabu Kanesaka (57) ABSTRACT

An X-ray equipment includes a movable carriage, an X-ray tube for irradiating an X-ray on a subject, and a cassette storage box for storing a cassette with a radiographic storage medium such as a film. In the X-ray equipment, when the cassette storage box is pulled and tilted, a gateway for the cassette is opened. When the cassette storage box is pushed back, the gateway is closed. The X-ray equipment further includes a storage box locking device for locking the cassette storage box in a state where the gateway is closed and for unlocking the cassette storage box when the locked state is released, and a locking release holding device for holding the storage box locking device in a released state.

2 Claims, 6 Drawing Sheets

X-RAY EQUIPMENT WITH CASSETTE STORAGE BOX LOCKING MEANS

BACKGROUND OF THE INVENTION AND RELATED ART STATEMENT

The present invention relates to an X-ray equipment used in, for example, a hospital. More specifically, the present invention relates to an X-ray equipment in which a cassette loaded with a radiographic storage medium such as a film is easily taken in and out of a cassette storage box where the cassette is stored.

Figure 8:
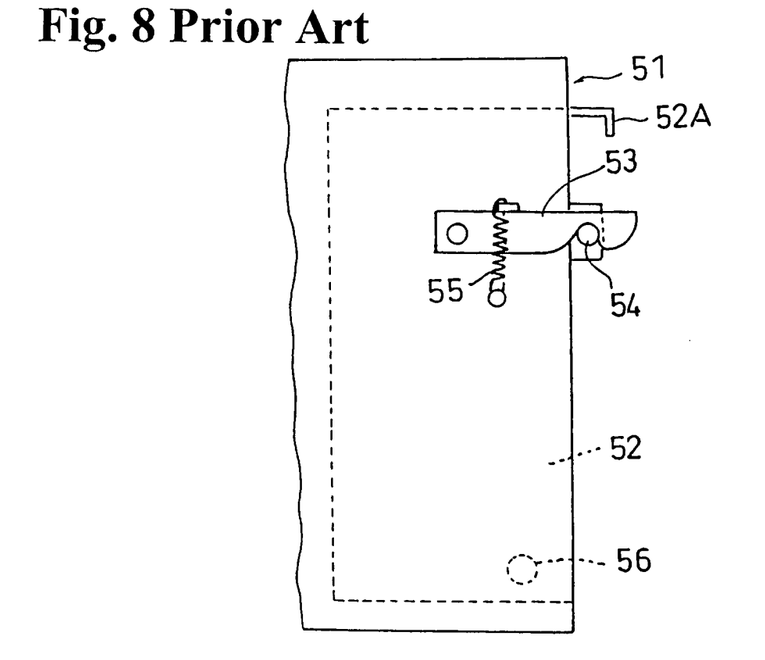
FIG. 8 is a partial side view showing a back end of a side surface of a carriage of a conventional X-ray equipment.
Figure 9:
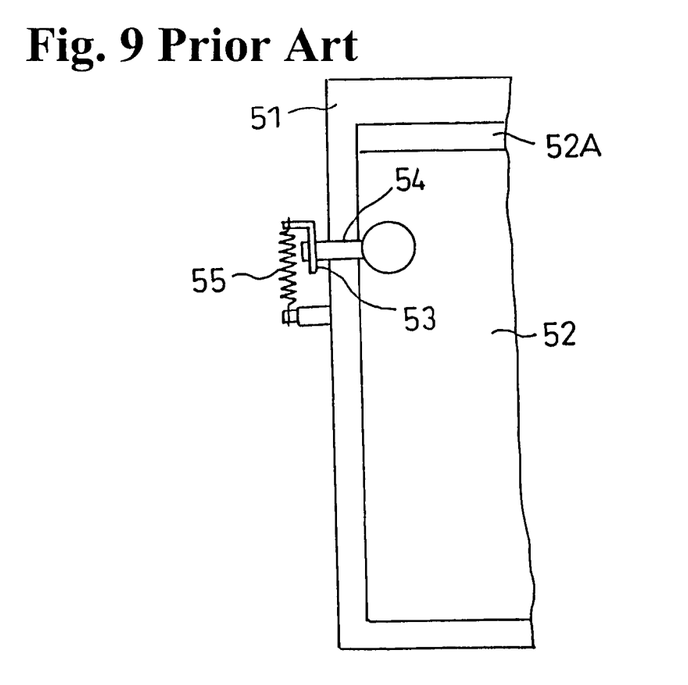
FIG. 9 is a partial back view showing a side of a back surface of the carriage of the conventional X-ray equipment.

As shown in FIGS. 8 and 9, in a conventional X-ray equipment, a cassette (not shown) loaded with a radiographic storage medium such as a film is stored in a cassette storage box 52. The cassette storage box 52 is mounted on a mobile carriage 51 where an X-ray tube (not shown) for irradiating X-ray on a subject (not shown) is equipped. When an X-ray picture is to be taken, the X-ray equipment is moved to a place where the X-ray picture is taken such as a hospital room, and an unused cassette is taken out of the cassette storage box 52 and the X-ray picture is taken.

When the cassette storage box 52 is pulled and tilted, a gateway for the cassette is opened. When the cassette storage box 52 is pushed back, the gateway is closed. As shown in FIG. 8, a hook 53 is rotatably supported on the carriage 51, and a pin 54 fixed to the cassette storage box 52 engages the hook 53, so that the cassette storage box 52 is locked (locked state) in a state that the gateway is closed. Also, the hook 53 is always urged downwardly with a spring 55 provided on the carriage 51.

Figure 10:
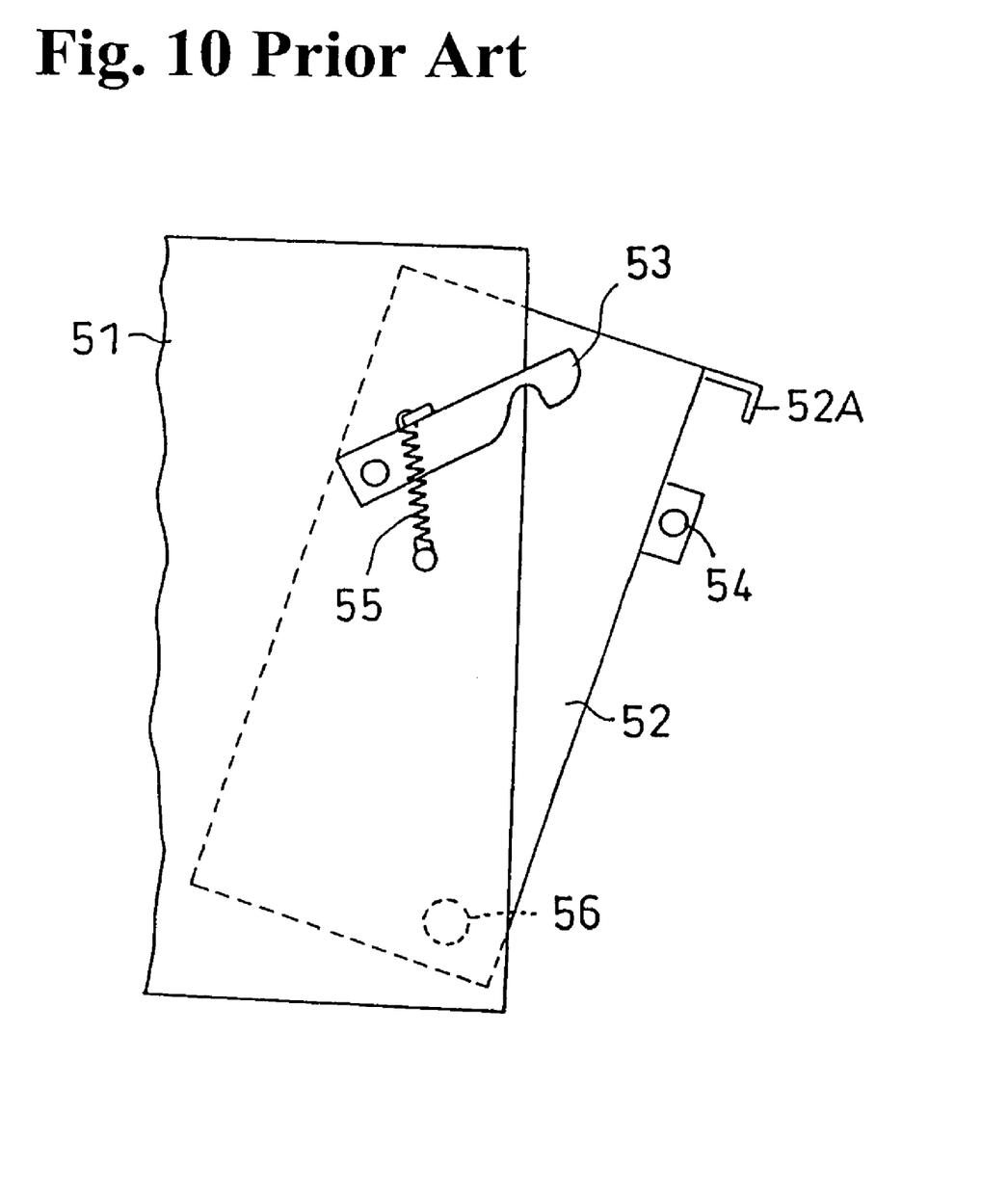
FIG. 10 is a partial side view showing a state in which a cassette storage box of the conventional X-ray equipment is pulled and tilted.

As shown in FIG. 10, when the gateway of the cassette storage box 52 is opened, a handle 52A of the cassette storage box 52 is pulled with one hand while the hook 53 is lifted up with the other hand. Accordingly, the cassette storage box 52 rotatably supported on a rotational axis 56 is pulled and tilted, and the gateway of the cassette is opened.

After the radiography is completed, the exposed cassette is returned to the cassette storage box 52, and the gateway of the cassette storage box 52 is closed. When the gateway of the cassette storage box 52 is closed, the handle 52A of the cassette storage box 52 is pushed with one hand while the hook 53 is lifted with the other hand. Then, the cassette storage box 52 supported on the rotational axis 56 is returned, so that the gateway is closed. After the gateway of the cassette storage box 52 is closed as described above, the carriage 51 travels to move the X-ray equipment to another place.

In the conventional X-ray equipment described above, it is not easy for an operator to take the cassette in and out of the cassette storage box 52. That is, when the gateway of the cassette storage box 52 is opened or closed, the operator has to pull and tilt the cassette storage box 52 or push back the cassette storage box 52 with one hand while the operator needs to lift up the hook 53 with the other hand in order to keep releasing the hook 53 from the locked state. Therefore, when the gateway is opened or closed, the operator has to use both hands at the same time.

In view of the problem described above, the present invention has been made, and an object of the present invention is to provide an X-ray equipment in which a cassette can be easily taken in and out of the cassette storage box.

Further objects and advantages of the invention will be apparent from the following description of the invention.

SUMMARY OF INVENTION

In order to achieve the objects described above, according to the first aspect of the present invention, an X-ray equipment includes a movable carriage; an X-ray tube for irradiating an X-ray on a subject; and a cassette storage box for storing a cassette loaded with a radiographic storage medium such as a film. In the X-ray equipment, when the cassette storage box is pulled and tilted, a gateway for the cassette is opened. When the cassette storage box is pushed back, the gateway is closed. The X-ray equipment further includes storage box locking means for locking the cassette storage box in a state where the gateway is closed and for unlocking the cassette storage box when the locked state is released; and locking release holding means for holding the storage box locking means in a released state.

In the first aspect of the present invention, when the gateway of the cassette storage box is opened, the storage box locking means is released from the locked state and is held in the released state by the locking release holding means. Then, the cassette storage box is pulled and tilted by one hand, so that the gateway is opened. When the gateway of the cassette storage box is closed, the storage box locking means is released again and held in the released state by the locking release holding means. Then, the cassette storage box is pushed back by one hand, so that the gateway is closed.

In the first aspect of the present invention, whenever the gateway of the cassette storage box is opened or closed, the locking release holding means holds the storage box locking means in the released state. Accordingly, an operator does not need to hold the released state of the storage box locking means, so that the cassette storage box can be pulled or pushed with one hand. As a result, the cassette can be easily taken in and out of the cassette storage box.

According to the second aspect of the present invention, the X-ray equipment of the first aspect further includes auto-lock switching means for switching the storage box locking means from the released state to the locked state when the cassette storage box is pushed back.

In the second aspect of the present invention, the auto-lock switching means switches the storage box locking means from the released state to the locked state in conjunction with a movement of the cassette storage box when the cassette storage box is pushed back to close the gateway. Therefore, the storage box locking means automatically switches from the released state to the locked state. As a result, the cassette can be easily taken in and out of the cassette storage box.

According to the third aspect of the present invention, in the X-ray equipment of the second aspect further, the storage box locking means includes a pin and a hook. When the hook is rotated in one direction and engages the pin, the locked state is obtained. When the hook is rotated in the opposite direction and moves away from the pin, the locked state is released. Further, the locking release holding means includes an elastic member for urging the hook in a direction that the hook engages the pin in the locked state, and in a direction that the hook moves away from the pin in the released state. The elastic member urges the hook in the direction that the hook moves away from the pin, so that the storage box locking means is held in the released state.

Further, the auto-lock switching means includes a boss and a lever. When the storage box locking means is switched from the released state to the locked state, the boss pushes the lever to rotate, and the lever pushes the hook to rotate in one direction. The elastic member switches the urging direction from the direction that the hook moves away from the pin to the direction that the hook engages the pin.

According to the fourth aspect of the present invention, in the X-ray equipment of the second aspect, the storage box locking means includes a pin fixed on the cassette storage box and a hook rotatably supported on the carriage. The hook rotates in one direction to engage the pin, so that the storage box locking means is in the locked state. The hook rotates in the other direction to move away from the pin, so that the storage box locking means is in the released state. The locking release holding means includes a spring provided on the carriage for urging the hook in the direction that the hook engages the pin in the locked state, and in the direction that the hook moves away from the pin in the released state; a stopper provided on the hook; and an opening provided in the carriage for fitting the stopper therein so that the hook can rotate. The spring urges the hook to move away from the pin, and the hook stops at a point that the stopper abuts against an edge of the opening at a side far from the pin, so that the storage box locking means is held in the released state.

Further, according to the fourth aspect of the invention, the auto-lock switching means includes a boss fixed on the cassette storage box and a lever supported on the carriage and being rotatable when the boss pushes the lever in conjunction with the movement of the cassette storage box. When the cassette storage box is pushed back, the boss moves in conjunction with the cassette storage box, and pushes the lever to rotate. Then, the lever pushes the hook to rotate in one direction and engages the pin. Also, the spring switches the urging direction from the direction that the hook moves away from the pin to the direction that the hook engages the pin, so that the storage box locking means can switch from the released state to the locked state.

In the third and fourth aspects of the present invention, when the gateway of the cassette storage box is opened, the hook caught on the pin is rotated to the other side by a hand to release the hook from the pin. Accordingly, the elastic member (the spring in the fourth aspect) urges the hook to move away from the pin (in the fourth aspect, the stopper moves until the stopper abuts against the edge of the opening at the side away from the pin), and the hook is held away from the pin. As a result, the storage box locking means is held in the released state. Then, the cassette storage box is pulled and tilted with one hand to open the gateway.

In the third and fourth aspects of the present invention, when the gateway of the cassette storage box is closed, the cassette storage box is pushed back with one hand, so that the gateway of the cassette is closed. At the same time, the boss moving in conjunction with the cassette storage box pushes the lever to rotate and push the hook, so that the hook rotates in one direction and engages the pin. Also, the elastic member (the spring in the fourth aspect) switches the urging direction from the direction that the hook engages the pin to the direction that the hook moves away from the pin, so that the storage box locking means can automatically switch from the locked state to the released state.

In the third and fourth aspects of the present invention, the storage box locking means, the locking release holding means, and the auto-lock switching means are all formed of simple mechanisms, and can be operated without power such as an electric current source.

DETAILED DESCRIPTION OF PREFERRED EMBODIMENTS

Figure 1:
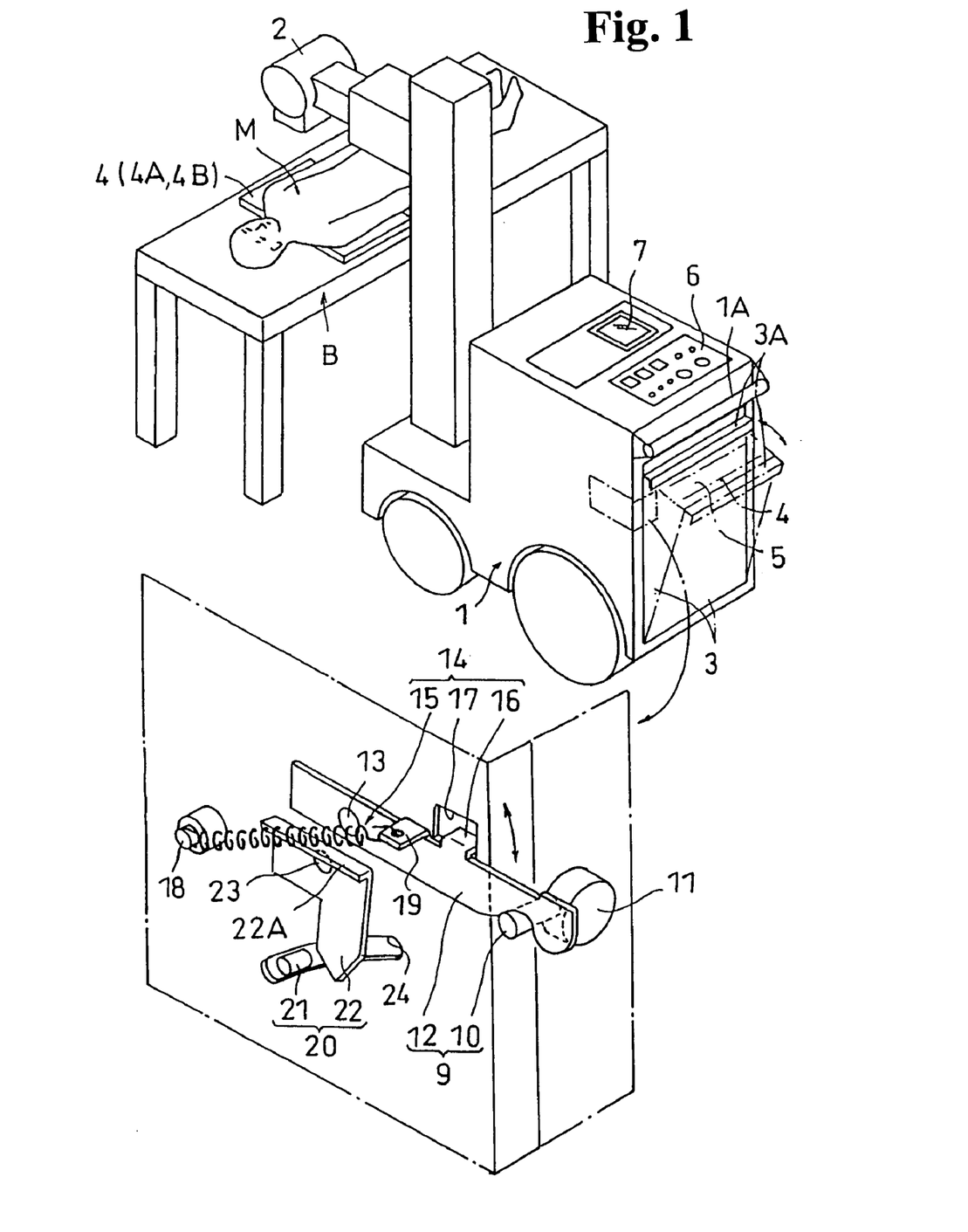
FIG. 1 is a perspective view showing an X-ray equipment according to an embodiment of the present invention.
Figure 2:
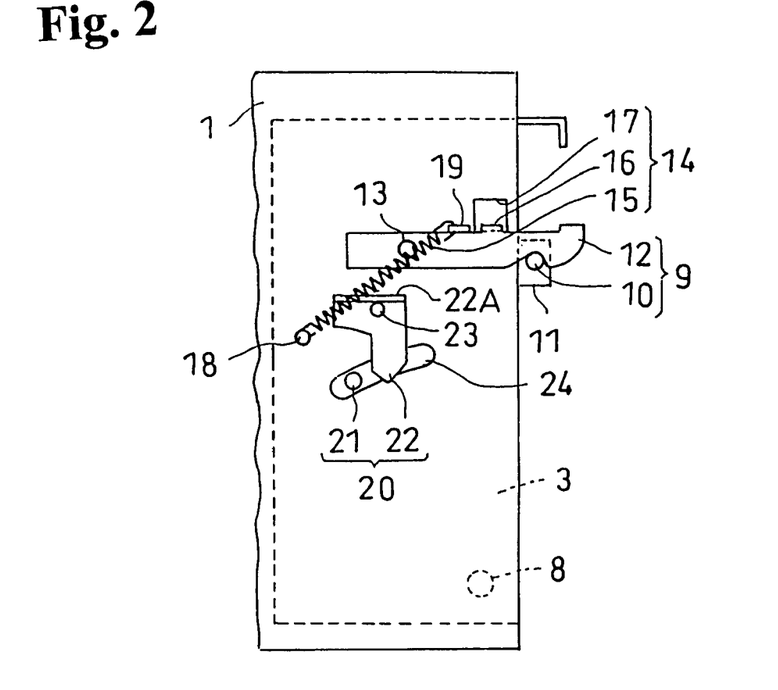
FIG. 2 is a partial side view showing a back end of a side surface of a carriage of the X-ray equipment according to the embodiment.
Figure 3:
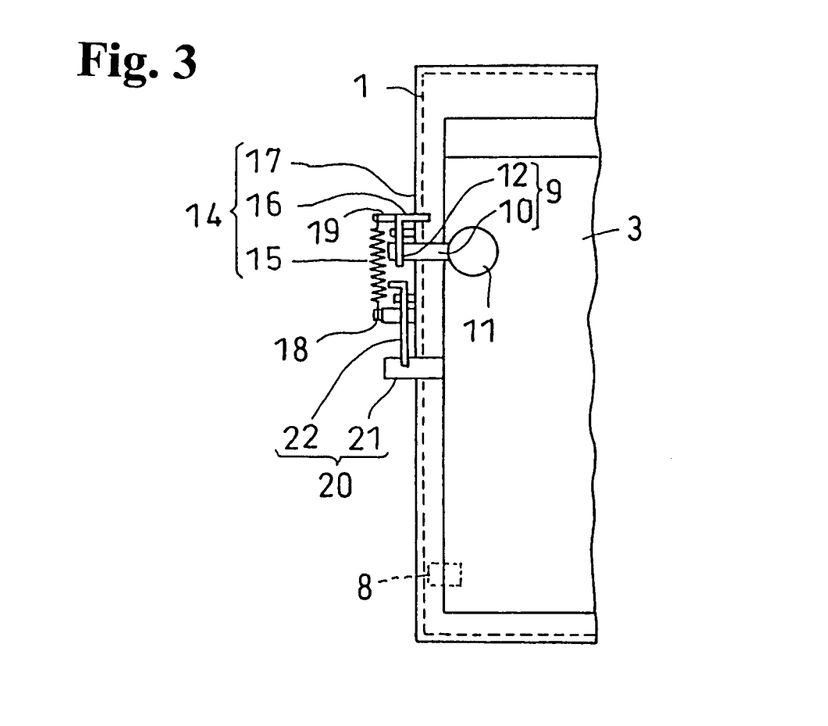
FIG. 3 is a partial rear view showing one side of a back surface of the carriage of the X-ray equipment according to the embodiment.

Hereunder, embodiments of an X-ray equipment of the present invention will be explained with reference to the accompanying drawings. FIG. 1 is a perspective view showing an X-ray equipment according to an embodiment, FIG. 2 is a partial side view showing a back end of a side surface of a carriage of the X-ray equipment, and FIG. 3 is a partial back view showing a side of a back surface of the carriage of the X-ray equipment.

The X-ray equipment of the embodiment includes a self-propelled movable carriage 1; a rechargeable battery (not shown) disposed in the carriage 1 as a power source; an X-ray tube 2 disposed between a front end and a center of the carriage 1 for irradiating X-ray on a subject M; and a high-voltage electric source (not shown) for supplying a high voltage and an electric current to the X-ray tube 2. A cassette storage box 3 is disposed at a back end of the carriage 1 for storing a cassette 4 loaded with a radiographic storage medium such as a film. Also, on a top surface of the carriage 1, there are provided an operation panel 6 for setting a filming condition and for inputting an instruction of X-ray irradiation, and a display monitor 7 for displaying various types of information such as the filming condition and data of the subject M.

In the X-ray equipment of the embodiment, the carriage 1 moves as follows. When an operator (technician) grips a handgrip (driving handle) 1A including a pressure sensor (not shown) and pushes or pulls the carriage 1, the pressure sensor detects a pressure on the handgrip 1A. Accordingly, an electric motor (not shown) rotates in a direction at a speed according to the detected pressure, so that wheels of the carriage 1 rotate and the carriage 1 electrically moves.

As indicated by hidden lines in FIG. 1, the cassette storage box 3 is attached to the carriage 1 rotatably around an axis 8, so that a gateway 5 for the cassette 4 is opened when the cassette storage box 3 is pulled and tilted, and the gateway 5 is closed when the cassette storage box 3 is pushed back. A storage box locking apparatus 9, or storage box locking means, is provided for holding the cassette storage box 3 in a locked state (locked state) while the gateway 5 of the cassette 4 of the cassette storage box 3 is closed as shown with solid lines in FIG. 1.

In the equipment of the embodiment, the storage box locking apparatus 9 includes a pin 10 and a hook 12. The pin 10 is fixed to a back surface of the cassette storage box 3 at an upper left end through a base 11 with a longitudinal direction thereof aligned in a horizontal direction of the carriage 1. The hook 12 is supported on a side surface of the carriage 1 rotatable around an axis 13 with a longitudinal direction thereof aligned in an extending direction of the carriage 1. The hook 12 rotates clockwise (one direction) to move downwardly, and engages the pin 10 so that the storage box locking apparatus 9 is in the locked state as shown in FIGS. 2 and 3.

Figure 4:
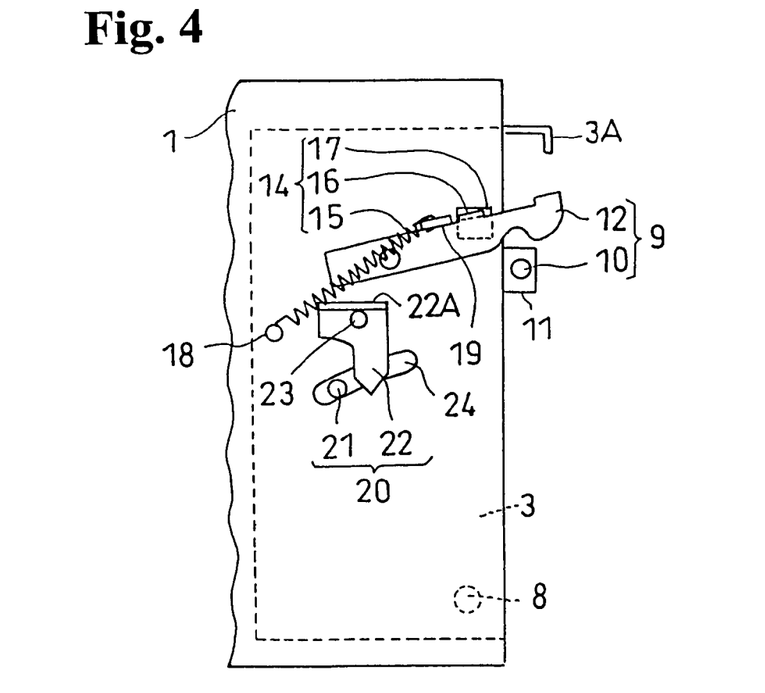
FIG. 4 is a partial side view showing a state in which a storage box locking device of the X-ray equipment is held in a released state.
Figure 5:
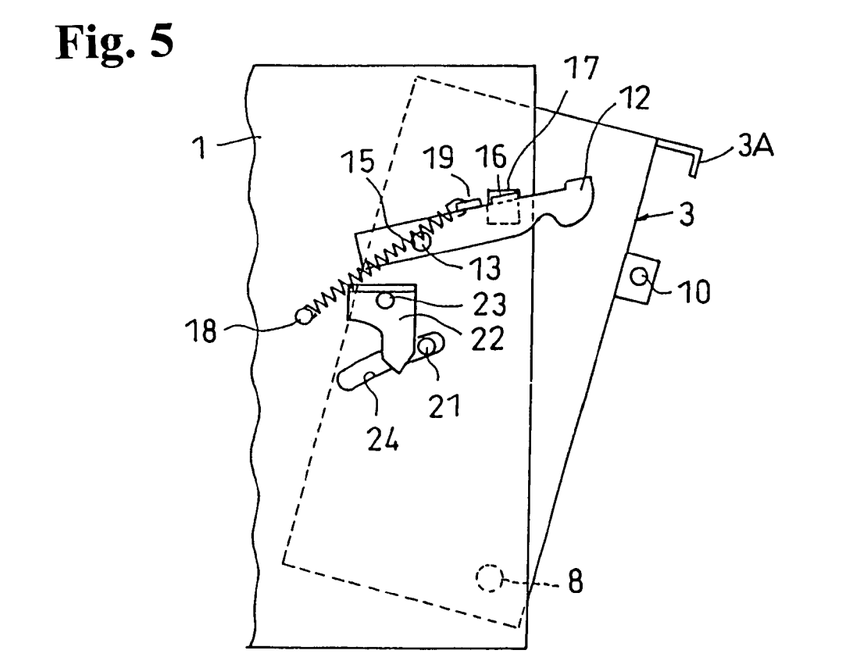
FIG. 5 is a partial side view showing a state in which a cassette storage box of the X-ray equipment is pulled and tilted.

On the other hand, the hook 12 rotates counterclockwise (the other direction) to move upwardly, and disengages from the pin 10 so that the storage box locking apparatus 9 is in the released state as shown in FIG. 4. As shown in FIG. 5, in the released state, the gateway 5 for the cassette 4 is opened when the cassette storage box 3 is pulled and tilted.

Also, in the equipment of the embodiment, a locking release holding apparatus 14, or locking release holding means, is provided in the storage box locking apparatus 9 for holding the cassette storage box 3 in the released state. The locking release holding apparatus 14 includes a spring 15, a stopper 16 and an opening 17. The spring 15 is provided on the side surface of the carriage 1 for urging the hook 12 in a direction that the hook 12 engages the pin 10 in the locked state, and for urging the hook 12 in a direction that the hook 12 moves away from the pin 10 in the released state. The stopper 16 is attached to the hook 12. The opening 17 is provided in the side surface of the carriage 1 for receiving the stopper 16 so that the hook 12 can rotate.

The spring 15 is placed between an immovable spring engagement projection 18 formed on the side surface of the carriage 1 and a movable spring engagement piece 19 formed at the middle of the hook 12 and moving together with the rotation of the hook 12. When the hook 12 engages the pin 10, the axis 13 of the hook 12 is located above the spring 15, and when the hook 12 is away from the pin 10, the axis 13 of the hook 12 is located below the spring 15. As a result, the spring 15 switches the direction of urging the hook 12 between the locked state and the released state. In the locked state, the spring 15 urges the hook 12 clockwise so that the hook 12 engages the pin 10, and in the released state, the spring 15 urges the hook 12 counterclockwise so that the hook 12 moves away from the pin 10.

As shown in FIG. 4, the spring 15 urges the hook 12 counterclockwise to move away from the pin 10 until the stopper 16 abuts against an edge of the opening 17 at a side away from the pin, and the hook 12 stops at the position so that the storage box locking apparatus 9 is held in the released state.

In the equipment of the embodiment, a self-locking switching apparatus 20, or self-locking switching means, is provided for switching the storage box locking apparatus 9 from the released state to the locked state in conjunction with a movement of the cassette storage box 3 when the cassette storage box 3 is pushed back. The self-locking switching apparatus 20 includes a boss 21 and a lever 22. The boss is fixed on the side surface of the cassette storage box 3. The lever 22 is supported on the side surface of the carriage 1 rotatable around the axis 23 when the boss 21 moves in conjunction with the movement of the cassette storage box 3 to push the lever 22.

Figure 6A:
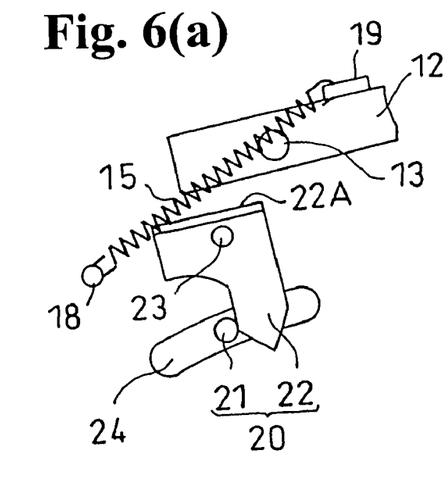
FIGS. 6(a) and 6(b) are explanatory drawings showing an operation of a self-locking switching device of the X-ray equipment.

An arc-shaped opening 24 is provided in the side surface of the carriage 1 for allowing the boss 21 to move in conjunction with the movement of the cassette storage box 3. As a result, when the cassette storage box 3 is pulled and tilted as shown in FIG. 5, the boss 21 moves in the opening 24 in a longitudinal direction thereof. Then, the boss 21 passes the lever 22 while pushing up the same as shown in FIG. 6(a). After the boss 21 passes the lever 22, the lever 22 returns to the previous position as shown in FIG. 4, and the boss 21 is situated at a backside of the lever 22.

Figure 6B:
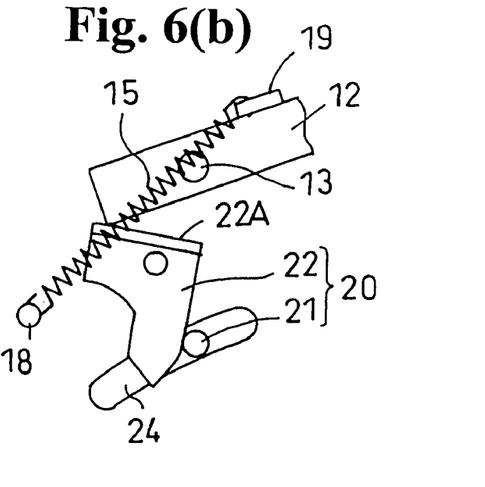

As shown in FIG. 6(b), the storage box locking apparatus 9 is switched from the released state to the locked state in the following process. When the cassette storage box 3 is pushed back, the boss 21 is moved in the opposite direction along a long side in the opening 24. When a top side 22A of the lever 22 is pushed by the boss 21 and rotated, the hook 12 is pushed by the top side 22A and rotated clockwise (one direction). Accordingly, the hook 12 engages the pin 10, and the force of the spring 15 is switched from the direction that the hook 12 moves away from the pin 10 to the direction in which the hook 12 engages the pin 10.

In the equipment of the embodiment, a cover (not shown) is placed on the side surface of the carriage 1 from above. Usually, the storage box locking apparatus 9, locking release holding apparatus 14, and self-locking switching apparatus 20 are not exposed except the pin 10 and base 11.

Figure 7:
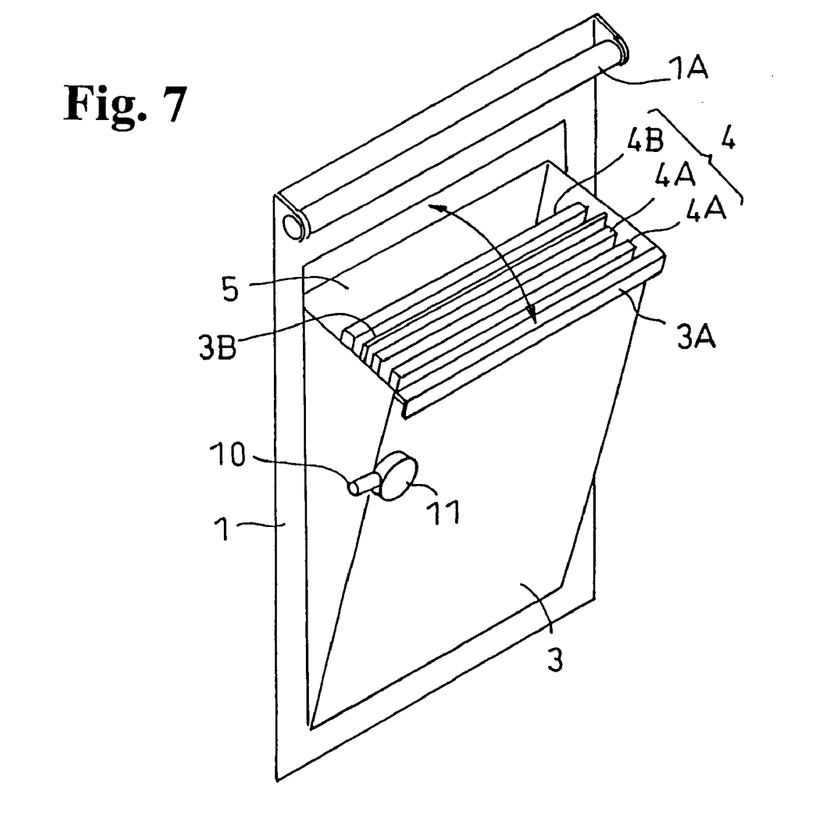
FIG. 7 is a partial perspective view showing a state in which a gateway of the cassette storage box of the X-ray equipment is opened.

An operation of opening and closing the gateway 5 of the cassette storage box 3 will be explained next in a case of performing X-ray photography. When an X-ray picture is taken, the carriage 1 is used to move the X-ray equipment to a place where the X-ray is taken such as a patient room. At the place, the gateway 5 of the cassette storage box 3 is opened. That is, the hook 12 engaging the pin 10 is rotated (lifted up) counterclockwise to move away from the pin 10 with a hand. Accordingly, as shown in FIG. 4, the spring 15 urges the hook 12 counterclockwise to move until the stopper 16 abuts against the edge of the opening 17 at the side away from the pin 10, and the hook 12 is disengaged from the pin 10. The storage box locking apparatus 9 maintains the released state. A handle 3A of the cassette storage box 3 is pulled out with a hand, and the cassette storage box 3 is tilted, so that the gateway 5 is opened as shown in FIG. 7.

The cassette 4 placed at a front side of a partition 3B is taken out of the gateway 5 of the cassette storage box 3 as an unexposed cassette 4A, and placed under the subject M on the bed B, as shown in FIG. 1. Then, the x-ray tube 2 radiates the x-ray to take the x-ray picture. The exposed cassette 4 is returned to a rear side of the partition 3B through the gateway 5 as an exposed cassette 4B.

Next, the gateway 5 of the cassette storage box 3 is closed, i.e. the handle 3A of the cassette storage box 3 is pushed back with a hand. Accordingly, the cassette storage box 3 is returned into the carriage 1 and the gateway 5 of the cassette 4 is closed. At the same time, the boss 21 moving with the cassette storage box 3 pushes the lever 23 to rotate and push the hook 12. Accordingly, the hook 12 is rotated clockwise and engages the pin 10. The spring 15 switches the urging direction from the direction that the hook 12 moves away the pin 10 to the direction that the hook 12 engages the pin 10. As a result, the cassette storage box 3 is automatically switched from the released state to the locked state.

As described above, in the X-ray equipment of the invention, the locking release holding apparatus 14 maintains the released state of the storage box locking apparatus 9 when the gateway 5 of the cassette storage box 3 is opened or closed. Therefore, an operator does not need to hold the released state of the storage box locking apparatus 9. It is possible to push or pull the cassette storage box 3 with a hand to close or open the gateway 5 for the cassette 4. As a result, the cassette 4 can be easily taken in and out of the cassette storage box 3.

In the X-ray equipment of the invention, when the gateway 5 of the cassette 4 of the cassette storage box 3 is closed, the storage box locking apparatus 9 held in the released state automatically switches to the locked state in conjunction with the movement of the cassette storage box 3 that is pushed back. Therefore, the cassette 4 can be easily taken in and out of the cassette storage box 3. Further, the storage box locking apparatus 9, the locking release holding apparatus 14, and the self-locking switching apparatus 20 are formed of simple mechanisms, and can be operated without using a power source such as an electric current source.

The present invention is not limited to the above-mentioned embodiments, and can be modified as follows. In the X-ray equipment of the present embodiment, the whole portion or a part of the operation panel 6 or the display monitor 7 may be a mobile terminal, and may be placed on the top surface of the carriage 1 as a portable device.

The storage box locking apparatus 9, the locking release holding apparatus 14, and the self-locking switching apparatus 20 are not limited to the embodiments, and may be modified. For example, in the embodiments, the coil spring 15 is provided as the elastic member for urging the hook 12. Alternatively, a spring such as a leaf spring or a spiral spring, or a rubber member can be used as the elastic member.

As described above, according to the X-ray equipment of the present invention, when the gateway of the cassette of the cassette storage box is opened and closed, the storage box locking means is held in the released state with the locking release holding means. Therefore, the operator does not need to hold the storage box locking means, so that the cassette storage box can be pulled or pushed to open or close the gateway of the cassette with one hand. As a result, the cassette can be easily taken in and out of the cassette storage box.

While the invention has been explained with reference to the specific embodiments of the invention, the explanation is illustrative and the invention is limited only by the appended claims.

What is claimed is:

1. An X-ray equipment comprising:
   a carriage,
   an X-ray tube mounted on the carriage for irradiating X-rays,
   a cassette storage box pivotally attached to the carriage for storing a cassette with a radiographic storage medium,
   storage box locking means engaging the cassette storage box for locking the cassette storage box in a locked state, and
   locking release holding means attached to the storage box locking means for holding the storage box locking means in a released state so that the storage box locking means is released from the locked state,
   wherein said locking release holding means includes an elastic member for urging the storage box locking means in the locked state when the storage box locking means is locked, and for urging the storage box locking means in the released state when the storage box locking means is released.

2. An X-ray equipment according to claim 1, wherein said locking release holding means further includes means for limiting movement of the storage box locking means between a release position and a lock position of the storage box.

* * * * *